United States Patent [19]  
Sanford

[11] 4,041,951  
[45] Aug. 16, 1977

[54] ABSORPTIVE STRUCTURE HAVING IMPROVED SURFACE DRYNESS AND IMPROVED RESISTANCE TO REWETTING IN-USE

[75] Inventor: Lawrence H. Sanford, Cincinnati, Ohio

[73] Assignee: The Procter & Gamble Company, Cincinnati, Ohio

[21] Appl. No.: 663,022

[22] Filed: Mar. 2, 1976

[51] Int. Cl.$^2$ ............................................. A61F 13/16
[52] U.S. Cl. ................................. 128/287; 128/290 W
[58] Field of Search .......... 128/284, 287, 296, 290 W, 128/290 R

[56] References Cited

U.S. PATENT DOCUMENTS

| 2,788,003 | 4/1957 | Morin | 128/284 |
|---|---|---|---|
| 2,916,037 | 12/1959 | Hansen | 128/284 |
| 3,065,751 | 11/1962 | Gobbo, Sr. et al. | 128/287 |
| 3,315,676 | 4/1967 | Cooper | 128/287 |
| 3,468,311 | 9/1969 | Gallagher | 128/296 |
| 3,616,157 | 10/1971 | Smith | 428/171 |
| 3,645,264 | 2/1972 | Gallagher | 128/296 |
| 3,721,242 | 3/1973 | Krusko | 128/287 |
| 3,814,101 | 6/1974 | Kozak | 128/287 |
| 3,908,659 | 9/1975 | Wehrmeyer et al. | 128/287 |
| 3,927,673 | 12/1975 | Taylor | 128/287 |
| 3,929,135 | 12/1975 | Thompson | 128/287 |
| 3,934,588 | 1/1976 | Mesek et al. | 128/290 W |
| 3,965,906 | 6/1976 | Karami | 128/287 |
| Re. 26,151 | 1/1967 | Duncan et al. | 128/284 |

Primary Examiner—Aldrich F. Medbery  
Attorney, Agent, or Firm—E. Kelly Linman; Fredrick H. Braun; John V. Gorman

[57] ABSTRACT

Absorptive devices, such as disposable diapers, presenting a dry surface feel to the user. In a particularly preferred embodiment of the present invention, a substantially planar, moisture absorbent layer is disposed between a soft and bulky, wearer contacting, moisture-pervious topsheet and a moisture-resistant backing sheet to form a disposable diaper. The topsheet preferably comprises an integral structure containing a multiplicity of depressed areas which intimately contact the uppermost surface of a substantially planar, moisture absorbent layer, while the non-depressed areas of the topsheet contact the wearer's skin in-use. Due to the wet resilience and increased overall caliper of the topsheet, the non-depressed areas, which are of substantially the same density as the depressed areas, tend to isolate the wearer's skin from moisture contained within the moisture absorbent layer, thereby providing improved surface dryness and improved resistance to rewetting when the structure is temporarily subjected to pressure resulting from the wearer's body movements.

12 Claims, 7 Drawing Figures

ABSORPTIVE STRUCTURE HAVING IMPROVED SURFACE DRYNESS AND IMPROVED RESISTANCE TO REWETTING IN-USE

BACKGROUND OF THE INVENTION

The present invention relates to topsheets for absorptive devices such as diapers, sanitary napkins, bed pads, incontinent pads, towels, bandages and the like, and more particularly, to absorptive structures which freely allow fluid to pass into the interior of an absorptive device but which tend to inhibit the reverse flow of fluid. A topsheet or facing sheet is the portion of an absorptive device which covers one face of the absorbent element of an absorptive device and which typically contacts the skin of the person using the absorptive device.

Absorptive devices are articles of manufacture designed to receive and retain fluid discharges from the wearer's body within an absorbent element of the absorptive device. Absorptive devices such as diapers, sanitary napkins, catamenial tampons, bed pads, incontinent pads, towels, bandages and the like are well known articles of commerce. In recent times, single use disposable absorptive devices have significantly replaced permanent absorptive devices which are designed to be laundered and reused. While the improved absorptive structure of the present invention can be used with reusable absorptive devices, it finds greatest utility when utilized with disposable absorptive devices and will be discussed in that context.

Disposable absorptive devices comprising an absorbent pad covered with a topsheet which contacts the body are well known. Covering the outer portion of the absorptive device with a moisture-resistant or fluid-impermeable backsheet to prevent absorbed fluids from leaking out of the absorptive device and soiling clothing, bed clothes, etc. is equally well known. The absorbent pad component of disposable absorptive devices can comprise well known materials such as creped cellulose wadding, air-laid felt, or the like. The fluid-impermeable backsheet can comprise any of various materials well known in the art such as polyethylene film.

One of the principle disadvantages of conventional absorptive devices is the maceration of the skin caused by prolonged contact with absorbed fluids. One especially common manifestation of this maceration is diaper rash generally occurring about the base of the trunk of infants. In order to minimize the effect of prolonged liquid contact with the skin, absorptive devices such as diapers have been produced with the body contacting topsheet thereof designed to exhibit a greater degree of surface dryness. For example, U.S. Pat. No. 3,327,625 issued to Johnson on Mar. 1, 1966, teaches the use of a hydrophobic material in the crotch area of the diaper to cause moisture to wick away from the skin of an infant wearer and thereby provide a substantially dry surface in contact with the infant's skin. U.S. Pat. No. Re. 26,151 issued to Duncan et al. on Jan. 31, 1967, teaches the use of porous, hydrophobic nonwoven fabrics as topsheets. U.S. Pat. No. 2,916,037 issued to Hansen on Dec. 8, 1959, is a further example of the use of a nonwoven topsheet.

U.S. Pat. No. 3,814,191 issued to Kozak on June 4, 1974, attacks the problem of a wet topsheet in a manner slightly different from the use of hydrophobic nonwoven materials. Kozak suggests a topsheet of a non-fibrous, hydrophobic film which is provided with a plurality of valvular slits which restrict the reverse flow of liquid from the absorbent element of the device. U.S. Pat. No. 3,929,135, issued to Thompson on Dec. 30, 1975, suggests a topsheet of liquid-impermeable material provided with tapered capillaries, said capillaries having a base in the plane of the topsheet and an apex remote from the plane of said topsheet.

U.S. Pat. No. 3,934,588 issued to Mesek et al. on Jan. 27, 1976, suggests a topsheet provided with areas of preferential liquid flow surrounded by areas of increased water repellancy relative to the areas of preferential liquid flow. The areas of preferential liquid flow are, in preferred embodiments, in the form of thinned areas, areas of increased wettability or areas of normal wettability surrounded by water repellant borders. The preferential liquid flow areas are spread over at least the central portion of the facing layer to direct layer to the absorbent pad.

SUMMARY OF THE INVENTION

In a particularly preferred embodiment of the present invention, a disposable diaper having a substantially planar, moisture absorbent layer disposed between a soft and bulky, wearer-contacting, moisture-pervious facing sheet and a moisture-resistant backing sheet is provided. The facing sheet or topsheet preferably comprises an integral structure containing a multiplicity of depressed areas which intimately contact the uppermost surface of the substantially planar absorbent layer in-use. The non-depressed areas of the topsheet, which are of substantially the same density as the depressed areas, contact the wearer's skin in use. Due to the increased overall caliper of the topsheet, the non-depressed areas tend to isolate the wearer's skin from moisture contained within the moisture absorbent layer, thereby providing improved surface dryness and improved resistance to rewetting. In a particularly preferred embodiment of the present invention, the topsheet is comprised of a substantially hydrophobic material exhibiting wet resilience, i.e., the structure tends to retain its inherent resiliency characteristics even when wetted. Accordingly, when the diaper structure is subjected to pressure which tends to temporarily collapse the three-dimensional character of the topsheet due to body movements of the wearer, thereby causing more intimate contact between the wearer's skin and the entire uppermost surface of the topsheet, the topsheet tends to resume its substantially three-dimensional character upon removal of the pressure. This tends to re-isolate the wearer's skin from the moist absorbent layer located immediately beneath the topsheet.

An absorbent structure of the present invention is an improvement over prior art absorbent structures in that it allows the free transfer of liquid discharged from the wearer's body into the absorbent element of the device and thereafter tends to isolate the wearer's skin from the fluids absorbed within the substantially planar, moisture absorbent element located beneath the topsheet. While directed primarily to single use, disposable absorptive devices such as disposable diapers, embodiments of the present invention can be used as a disposable liner with reusable absorptive devices such as cloth diapers, etc.

OBJECTS OF THE INVENTION

Accordingly, it is an object of the present invention to provide an absorptive structure which permits the free transfer of fluids discharged from the wearer's body into the absorbent element of the absorptive device and thereafter tends to isolate the wearer's skin from the fluids absorbed within the absorbent element.

It is a further object of the present invention to provide a topsheet for absorptive devices which presents to the user a soft and dry non-irritating surface.

It is still a further object of the present invention to provide a topsheet for a disposable diaper having decreased contact area with the wearer's skin in-use.

It is yet another object of the present invention to provide a three-dimensional topsheet structure exhibiting wet resilience, such that upon removal of pressure caused by body movements of the wearer, the structure again seeks an equilibrium which tends to isolate the wearer's skin from moisture contained within the substantially planar, absorbent core element.

Finally, it is an object of the present invention to provide method and apparatus for producing a three-dimensional topsheet of the present invention.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE PREFERRED EMBODIMENTS

The discussion that follows is primarily directed to the use of the invention as a unique moisture-pervious topsheet structure embodied in a disposable diaper. While this is contemplated as being a preferred use, it should be understood that the present invention also has substantial utility in a wide variety of absorptive devices, both disposable and reusable, such as sanitary napkins, catamenial tampons, bed pads, incontinent pads, towels, bandages and the like. The detailed description of the topsheet structure and its use in a disposable diaper will allow one skilled in the art to readily adapt the invention to other devices.

Figure 1:
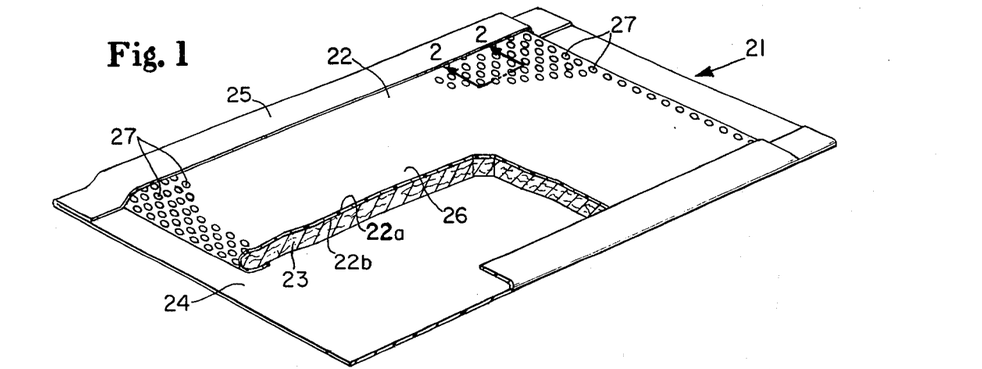
FIG. 1 is a perspective representation of an unfolded disposable diaper with portions of its components cut away.

FIG. 1 is a perspective view of a disposable diaper in an unfolded condition. Various layers have been cut away to more clearly show the structural details of this particular embodiment. The disposable diaper is referred to generally by the reference 21. A novel topsheet of the present invention is shown at 22. The other two major components of the disposable diaper 21 are the absorbent element or pad 23 and the backsheet 24. In general, the side flaps 25 of the backsheet 24 are folded so as to cover the edges of the absorbent pad 23 and topsheet 22. Topsheet 22 is generally folded to completely enclose the ends of absorbent pad 23. The drawing of diaper 21 in FIG. 1 is a simplified representation of a disposable diaper. A more detailed description of a preferred embodiment of a disposable diaper is contained in U.S. Pat. No. 26,151 which issued to Duncan et al. on Jan. 31, 1967, and which is hereby incorporated herein by reference.

A topsheet 22 of the present invention is preferably constructed from a moisture-pervious, generally hydrophobic, nonwoven fibrous web. In a particularly preferred embodiment, the web is comprised of approximately 65% staple length, polyester fibers having a denier of about 1.5, such as Kodel type 411 polyester fibers available from Tennessee Eastman Corporation of Kingsport, Tenn; approximately 15% staple length, crimped rayon fibers having a denier of approximately 1.5; and approximately 20% acrylic copolymer binder such as Celanese CPE 8335 available from the Celanese Corporation of Charlotte, N.C. As utilized herein, staple length fibers are those having a length of at least about ⅝ inches. The web is preferably carded, saturated with binder solution, dried and cured by means well known to those skilled in the art. The web has a basis weight in the range of about 18 to about 22 grams per square yard and a caliper of between about 7 and about 9 mils, as measured under a load of approximately 10 grams per square inch. The preferred web is further characterized by a minimum wet tensile strength of at least about 1000 grams per inch in the machine direction and at least about 140 grams per inch in the cross-machine direction.

Figure 5:
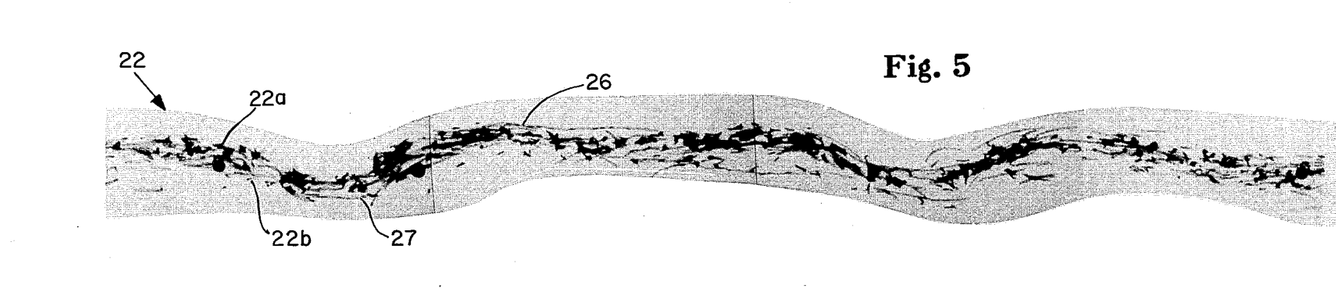
FIG. 5 is a cross-sectional photomicrograph, enlarged approximately 25 times actual size, of a preferred topsheet which has passed through the nip formed between a patterned steel embossing roll and a rubber back-up roll.

The web is preferably subjected to an embossing process similar to that utilized to emboss the extensible paper plies utilized in a multi-ply towelling structure disclosed in U.S. Pat. No. 3,414,459 which issued to Wells on Dec. 3, 1968, said patent being hereby incorporated herein by reference. The nonwoven web is preferably passed between a patterned steel roll having male projections thereon and a neoprene or silicone rubber coated roll having a P&J hardness between about 110 and about 150. In a particularly preferred embodiment, the steel embossing roll contains elliptical shaped knobs having an overall height of approximately 0.070 inches and measuring approximately 0.084 inches by approximately 0.042 inches at their apex, i.e., at their web contacting surface. The knobs are arranged in a diamond shaped array containing 6 knobs per inch in each row by 12 rows per inch. This results in a total of approximately 72 knobs per square inch, which corresponds to a total contact area with the web amounting to approximately 20% of the web's surface, as measured in the plane of the apex of the knobs. The web is preferably passed through a nip formed between the male embossing roll and the rubber back-up roll at an operating pressure of between about 400 and about 600 pounds per linear inch. FIG. 5 is a cross-sectional photomicrograph, enlarged approximately 25 times actual size, of a topsheet 22 embossed by the aforementioned process.

Figure 6:
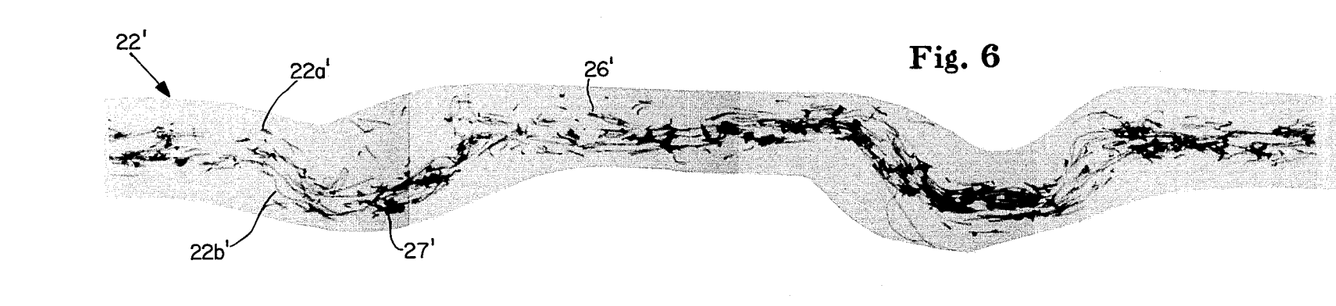
FIG. 6 is a cross-sectional view, similar to that of FIG. 5, of a preferred topsheet embossed between mating steel surfaces.

Although the rubber to steel embossing technique described above represents a preferred method of forming the topsheet, it is recognized that other means well known in the art may also be employed. For example, a similar embossed pattern may be produced in the topsheet by passing the nonwoven web between mating male and female rolls constructed of steel and having complementary embossing patterns provided at their peripheries. The latter technique would, of course, involve lower nip operating pressures, generally on the order of about 50 pounds per linear inch or less. FIG. 6 is a cross-sectional photomicrograph, similar to that of FIG. 5, of a topsheet embodiment 22' prepared utilizing mating male and female embossing patterns. The uppermost surface 22a' of the web was contacted by the male emboss pattern while the lowermost surface 22b' was contacted by the female emboss pattern. The resulting depressed areas 27' and non-depressed areas 26' are generally similar to those produced by the rubber to steel arrangement.

Figure 7:
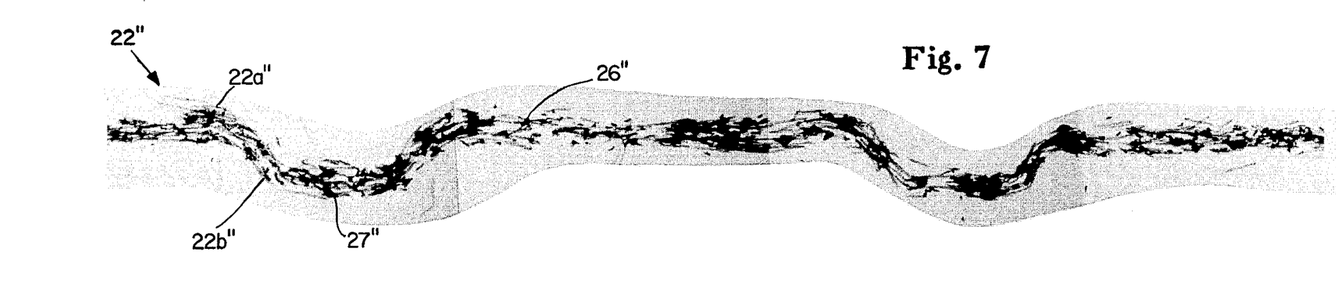
FIG. 7 is a cross-sectional view, similar to that of FIG. 5, of a preferred topsheet embossed between a patterned steel embossing roll and a paper back-up roll.

In yet another embodiment, a back-up roll comprised of paper is substituted for the rubber covered roll described above. In the latter situation, the paper roll is sufficiently soft to take on a permanent female emboss, thereby providing a mating surface for the patterned male roll. FIG. 7 is a cross-sectional photomicrograph, similar to that of FIG. 5, of a topsheet embodiment 22" prepared utilizing such a paper to steel arrangement. The uppermost surface 22a" of the web was contacted by the male emboss pattern on the steel roll while the lowermost surface 22b" was contacted by the paper roll. The resulting depressd areas 27" and non-depressed areas 26" are generally similar to those produced by the rubber to steel arrangement. Lower nip operating pressures are applied than with the rubber to steel arrangement described above, i.e., generally less than about 50 pounds per linear inch.

Furthermore, a topsheet of the present invention could be formed directly with depressed and non-depressed areas in its surface by web forming techniques well known in the art, rather than embossed, i.e., as by vacuum forming while the fibers are at a temperature above their softening points.

Figure 2:
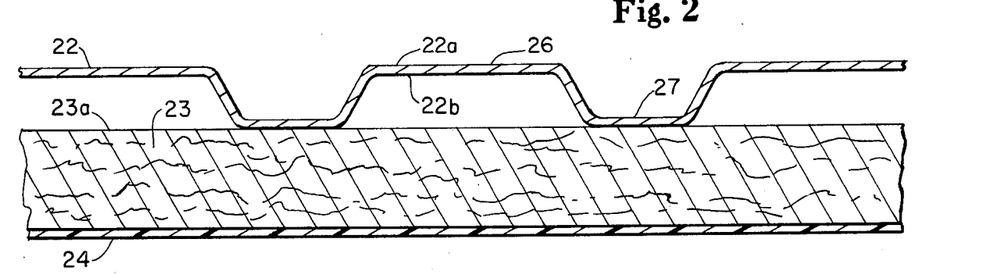
FIG. 2 is an enlarged cross-sectional view of the diaper illustrated in FIG. 1 taken along section line 2—2 in FIG. 1.

Embossing the carded, non-woven web as described above, produces a permanent, three-dimensional embossed pattern in the web, thereby greatly increasing its overall caliper. As shown in FIG. 2, the embossing pattern described in the above paragraphs produces a topsheet 22 exhibiting non-depressed areas 26 and depressed areas 27 corresponding to the male embossment points on the steel embossing roll. For example, a preferred web, as described herein, having a basis weight between about 18 and about 22 grams per square yard and an initial caliper prior to embossing of between about 7 and about 9 mils, as measured under a load of 10 grams per square inch, exhibits an overall caliper between about 13 and about 18 mils after embossing, as measured under a load of 10 grams per square inch.

It is critical to note, however, that although the embossing procedures described above produce a permanent set in a web of the present invention, they do not create patterned areas of densification in the web. This is more clearly illustrated not only in FIG. 2 but also in FIGS. 5, 6 and 7.

FIGS. 5 through 7 are photomicrographs, enlarged approximately 25 times actual size, of topsheets of the present invention after embossing. FIG. 5 is a cross-sectional photomicrograph of a topsheet 22 which has been passed between a steel and rubber roll arrangement, as described above. FIG. 6 shows a topsheet 22' processed by means of a steel to steel mating emboss arrangement, while FIG. 7 is illustrative of a topsheet 22" passed between a male embossing roll constructed of steel and a paper back-up roll. As is clearly apparent from the aforementioned photomicrographs, there is no densification of the depressed areas in relation to the non-depressed areas of the topsheet.

As is illustrated in FIG. 2, the topsheet 22 is preferably oriented on a disposable diaper structure 21 such that the non-depressed areas 26 are generally in contact with the wearer's skin while the depressed areas 27 contact the uppermost surface 23a of the absorbent pad element 23.

In a particularly preferred embodiment of the present invention, the surface of the embossed topsheet 22a which contacts the male embossing roll forms the wearer contacting surface of the diaper, while the surface 22b which contacts either the rubber coated roll or a female roll, depending upon the type of embossing process utilized, preferably forms the absorbent pad contacting surface of the topsheet. This orientation of the topsheet is generally preferred in order to maximize the isolating effect provided by the depressed areas 27 in the topsheet 22. The depressed areas 27 preferably constitute between about 10% and about 50% of the topsheet's total surface area. When the depressed areas 27 constitute less than about 10% of the topsheet's total surface area, there is a tendency for the non-depressed areas 26 to make intimate contact with the uppermost surface 23a of the absorbent pad element 23 at very low applied pressures, while at depressed areas greater than about 50%, there is a tendency of the wearer's skin to more readily conform to the depressed areas 27 due to a lack of support from the non-depressed areas 26.

Figure 3:
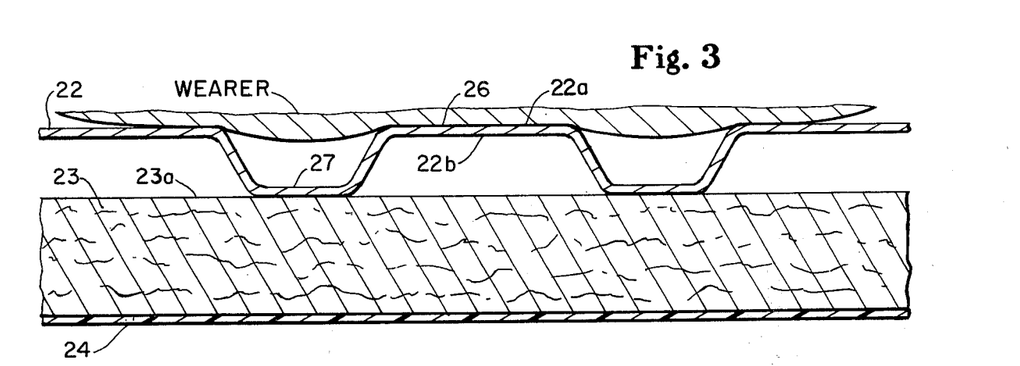
FIG. 3 is an enlarged cross-sectional illustration of a portion of a diaper of the present invention in contact with the surface of the wearer's skin under a substantially no-load condition.

FIG. 3 illustrates a portion of a disposable diaper of the present invention in contact with the skin of the wearer under an essentially no-load condition, i.e., the diaper is snugly secured about the wearer's waist, but the wearer is not exerting substantial pressure against the structure as by sitting on it. As is apparent from the illustration, the non-depressed areas 26 tend to isolate the wearer's skin from any direct contact with the moist absorbent core 23. Because the topsheet 22 is comprised of a hydrophobic material of substantially uniform density which contacts the moist hydrophilic absorbent core 23 along its uppermost surface 23a at the depressed areas 27, a favorable fluid flow gradient is created between the topsheet 22 and the absorbent core 23 at the embossed areas 27. Thus moisture discharged onto the uppermost surface of the topsheet 22a is readily transmitted either directly through the non-depressed areas 26 to the absorbent core 23 during periods of heavy flow or by capillary attraction to the depressed areas 27 which in turn transmit the fluid to the moist hydrophilic absorbent core 23 in contact therewith. The physical separation provided between the moist absorbent core 23 and the wearer's skin by virtue of the increased overall caliper of the topsheet 22 under a substantially no-load condition tends to provide a drier feeling surface next to the wearer's skin. In addition, applicant has determined that a three-dimensional topsheet of the present invention is generally perceived as being softer than substantially planar prior art topsheets utilized in similar applications. This is believed due to the improved bulk and flexibility of topsheets of the present invention.

Furthermore, because the topsheet 22 is generally hydrophobic in character, relative to the hydrophilic absorbent core 23, its overall density and its resiliency characteristics are relatively unaffected by wetting. Thus, even when pressures applied to the moist absorbent core 23 by movements of the wearer's body tend to temporarily collapse the three-dimensional structure of the topsheet 22, thereby causing moisture to re-enter the topsheet, the resilience of the topsheet causes it to resume its three-dimensional character upon removal of the applied pressures. When this occurs, the fluid is again rapidly drawn back into the moist absorbent core 23 by virtue of the favorable fluid flow gradient existing between the depressed areas 27 of the hydrophobic topsheet and the uppermost surface 23a of the moist hydrophilic absorbent pad element 23. This suction effect tends to draw moisture contained in the non-depressed areas 26 into the depressed areas 27, thereby re-establishing a dryer wearer-contacting surface in the non-depressed areas 26.

Figure 4:
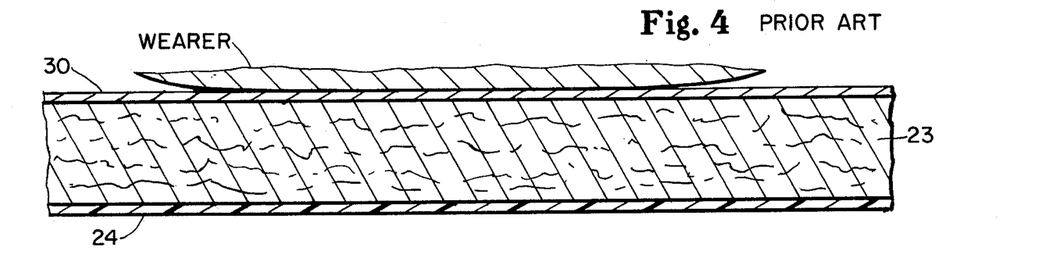
FIG. 4 is a cross-sectional illustration comparable to that of FIG. 3 illustrating a prior art disposable diaper under similar circumstances.

FIG. 4 illustrates the condition prevailing with a prior art disposable diaper structure which employs a topsheet 30 similar in all respects to the topsheet 22, but not having depressed areas 27 and non-depressed areas 26. Under a substantially no-load condition, there is very little physical separation between the wearer's skin and the uppermost surface 23a of the moist absorbent core 23. The physical isolation provided in the prior art structure is approximately equivalent to the caliper of the unembossed topsheet 30. Thus, the wearer's skin is much more easily rewetted upon the application of pressure due to movements of the wearer's body against the moist absorbent core 23. Furthermore, the substantially planar topsheet 30 cannot exhibit the same overall degree of caliper recovery as a three-dimensional topsheet of the present invention upon removal of temporarily applied pressures, since its maximum recovery is limited by its initial caliper. Thus a topsheet of the present invention is much more effective not only in initially establishing a dryer surface in contact with the wearer's skin due to greater physical isolation from the moist absorbent core, but also in re-establishing such a condition upon removal of temporarily applied pressures caused by body movements of the wearer.

Absorbent pad 23 of the disposable diaper exemplified in FIG. 1 can comprise materials commonly used in absorptive devices and well known in the art. A preferred form of suitable absorbent material for use in the pad 23 is comminuted wood pulp generally referred to as air felt. When air felt is used, a tissue paper envelope, preferably comprised of wet strength tissue paper, is normally utilized to encapsulate the air felt and provide an absorbent pad 23 exhibiting satisfactory in-use integrity. Other materials can also be used for the absorbent pad 23, such as a multiplicity of plies of creped cellulose wadding or any equivalent thereof.

As is clear from the foregoing description, it is preferable that the uppermost surface 23a of the absorbent pad 23 be substantially planar so as to avoid nesting of the absorbent material into intimate contact with the non-depressed areas 26 of the topsheet 22. Such nesting between the uppermost surface 23a of the absorbent pad 23 and the non-depressed areas 26 of the moisture-pervious topsheet 22 would obviously tend to minimize the physical isolation provided between the moist absorbent pad 23 and the non-depressed wearer-contacting surfaces 26 of the topsheet. Thus, the preferred areas of contact between the topsheet 22 and the uppermost surface 23a of the absorbent pad 23 are limited, at least under a substantially no-load condition, to the depressed areas 27 of the topsheet.

Moisture-resistant backsheet 24 can be of any material well known in the art. A preferred material is a moisture-impervious, low-density polyethylene 0.001 to 0.002 inches in thickness. If desired, a breathable, moisture-impervious backsheet containing apertured bosses, such as that described in Belgian Pat. No. 811,067 which issued to Sisson on Aug. 16, 1974, might also be employed.

The elements of a finished disposable diaper of the present invention — moisture-pervious generally hydrophobic topsheet 22, moisture-absorbent pad 23 and optional element such as moisture-impervious backsheet 24 — can be assembled into a practical, economical disposable diaper by means well known in the art. An example of such union into disposable diapers is admirably described in the hereinbefore incorporated U.S. Pat. No. Re. 26,151.

As noted, the topsheet 22 containing depressed areas 27 and non-depressed areas 26 of substantially uniform density has been described in terms of disposable diapers. Other absorptive devices well known in the art such as sanitary napkins, catamenial tampons, bed pads, incontinent pads, towels, bandages and the like can be advantageously constructed using a topsheet of the present invention. Specific examples of sanitary napkins and catamenial tampons wherein the topsheet of this invention can be used can be found in U.S. Pat. No. 3,800,797, issued to Tunc on Apr. 2, 1974, and U.S. Pat. No. 3,815,601, issued to Schaefer on June 11, 1974, both of which are hereby incorporated herein by reference.

In order to contribute to a better understanding of the present invention, and not by way of limitation, the following examples are provided.

EXAMPLE I

A disposable diaper generally in accordance with the teachings of U.S. Pat. No. Re. 26,151 was constructed utilizing a 1 mil thick polyethylene backsheet; a comminuted wood pulp absorbent core having a basis weight of approximately 0.2 grams per square inch and a density of approximately 0.15 grams per cubic centimeter, as measured under a load of approximately 0.5 pounds per square inch, encapsulated on both sides by a layer of wet strength envelope tissue having a basis weight of approximately 12.2 pounds per 3,000 square feet; and a topsheet of the present invention secured in superposed relation thereto. The topsheet was comprised of: approximately 65% staple length, bright, polyester fibers, having a denier of approximately 1.5, such as Kodel Type 411 polyester fibers available from Tennessee Eastman Corporation of Kingsport, Tenn.; approximately 15% staple length, crimped rayon fibers having a denier of approximately 1.5; and approximately 20% acrylic copolymer binder such as Celanese CPE 8335 available from the Celanese Corporation of Charlotte, N.C. The carded web was saturated with binder solution, dried and cured by means well known in the art to produce a finished web having a basis weight between about 18 and about 22 grams per square yard, an unembossed caliper between about 7 and about 9 mils, as measured under a load of approximately 10 grams per square inch, and a wet tensile strength of at least 1,000 grams per inch in the machine direction and at least 140 grams per inch in the cross-machine direction. The web was passed between a steel male embossing roll and a rubber back-up roll of the type described in detail in applicant's specification. The depressed areas in the resulting topsheet comprised approximately 20% of the topsheet's total surface area, as measured in the plane of the depressed areas. The embossment pattern comprised elliptical shaped, regularly spaced knobs totaling approximately 72 knobs per square inch. An operating pressure between about 400 and about 600 pounds per linear inch was employed to permanently emboss the web to an overall caliper of between about 13 and about 18 mils, as measured under a load of approximately 10 grams per square inch. The topsheet was installed on the diaper so that the surface of the web contacting the male embossment roll would be in contact with the wearer's skin in-use.

EXAMPLE II

A diaper structure identical to that of Example I was constructed, the only difference being that the topsheet was not subjected to any type of embossing operation prior to installation on the diaper.

In order to compare the surface wetness of the two diaper structures, a test designed to measure the amount of liquid which emerges from an absorbent structure through a topsheet to cause wetness on the surface of the topsheet was conducted. The amount of moisture drawn through the topsheet is termed "surface wetness" and serves as an estimate of how dry the wearer's skin would remain if placed in contact with the absorbent structure.

Briefly, the test comprises wetting a 4 inch by 4 inch sample of each diaper structure (after removal of the moisture impervious backsheet) with a simulated urine solution having a surface tension of approximately 45 dynes until the absorbent positions of the structure, i.e., the topsheet and the absorbent pad, including the envelope tissue, has reached a loading factor of 5.5, i.e., until the absorbent sample contains 5.5 grams of of simulated urine solution per gram of absorbent sample. A uniform pressure loading of 0.5 p.s.i. is applied to each sample for a period of 3 minutes so that the fluid is uniformly distributed throughout the sample. The pressure is momentarily removed, a preweighed sample of filter paper approximately 15 centimeters in diameter is inserted over the uppermost surface of the topsheet of the absorbent sample, and a predetermined pressure loading is reapplied to the sample for a period of 2 minutes. The filter paper is then removed and reweighed, and the amount of fluid absorbed by the filter paper is termed the "surface wetness" of the sample. The tests wer conducted at applied pressure loadings of 0.125 p.s.i., 0.25 p.s.i. and 0.5 p.s.i. to simulate varying in-use conditions ranging from slight surface contact between the topsheet surface and the wearer's skin to substantial pressure between the topsheet and the wearer's skin, such as when the wearer is sitting on the absorbent structure. As should thus be apparent, a lower "surface wetness" number is indicative of a dryer surface feel.

The data set forth in Table I hereinafter are based on an average of at least five individual samples:

| Applied Pressure Loading (Pounds per Sq. Inch.) | EXAMPLE I Surface Wetness (grams of simulated urine solution absorbed by filter paper) | EXAMPLE II Surface Wetness (grams of simulated urine solution absorbed by filter paper) |
| --- | --- | --- |
| 0.50 | 1.01 | 1.34 |
| 0.25 | 0.53 | 0.68 |
| 0.125 | 0.28 | 0.68 |

From the data set forth in Table I, it is manifest that a topsheet of the present invention, i.e., Example I, yields a considerable improvement in surface dryness over a substantially planar topsheet of identical composition when utilized in an otherwise identical absorbent structure.

The present invention has been described in particular detail with reference to a particularly preferred embodiment, and it is not intended to hereby limit to the particular embodiments shown or described. Many other variations of the present invention will be apparent to those skilled in the art.

What is claimed is:

1. In a disposable diaper having a substantially planar, moisture absorbent layer disposed between a soft and bulky, wearer-contacting, topsheet which is uniformly moisture-pervious along its entire surface and a moisture-resistant backing sheet, the improvement wherein said uniformly moisture-pervious topsheet comprises a wet resilient, integral structure containing a multiplicity of upwardly open depressed areas which intimately contact the uppermost surface of said substantially planar, moisture absorbent layer in-use, non-depressed areas, surrounding said depressed areas and contacting the wearer's skin in-use, said depressed and said non-depressed areas being of substantially uniform density throughout, said non-depressed areas tending to isolate the wearer's skin from moisture contained within said moisture-absorbent layer in-use, thereby providing improved surface dryness and improved resistance to rewetting.

2. The disposable diaper of claim 1, wherein said depressed areas in said topsheet are comprised of embossments.

3. The disposable diaper of claim 1, wherein said depressed areas comprise between about 10 percent and about 50 percent of the total surface area of said topsheet, as measured in the plane of said depressed areas.

4. The disposable diaper of claim 3 wherein said topsheet is comprised of a generally hydrophobic, nonwoven material, and said depressed areas are provided substantially throughout the entire surface of said topsheet.

5. The disposable diaper of claim 4, wherein said depressed areas are provided at least in those areas of said diaper which receive moisture discharged from the wearer's body.

6. The disposable diaper of claim 1, wherein said substantially planar, moisture absorbent layer is generally hydrophilic.

7. The disposable diaper of claim 6, wherein said substantially planar, moisture absorbent layer is comprised of a layer of fluffed cellulose wadding encapsulated on both surfaces by a layer of tissue paper.

8. The disposable diaper of claim 6, wherein said substantially planar, moisture absorbent layer is comprised of creped cellulose wadding.

9. In a body fluid absorbent structure comprising a substantially planar, generally hydrophilic moisture absorbent layer and a generally hydrophobic, soft and bulky, wearer-contacting, topsheet which is uniformly moisture-previous along its entire surface positioned in superposed relation thereto in-use, the improvement wherein said uniformly moisture-pervious topsheet comprises a wet resilient, integral structure containing a multiplicity of upwardly open depressed areas which intimately contact the uppermost surface of said substantially planar, moisture absorbent layer in-use, non-depressed areas surrounding said depressed areas and contacting the wearer's skin in-use, said depressed and said non-depressed areas being of substantially uniform density throughout, said non-depressed areas tending to isolate the wearer's skin from moisture contained within said moisture absorbent layer in-use, thereby providing improved surface dryness and improved resistance to rewetting.

10. The body fluid absorbent structure of claim 9, wherein said moisture-pervious topsheet comprises a disposable liner for a diaper.

11. The body fluid absorbent structure of claim 9, wherein said topsheet is comprised of a generally hydrophobic, non-woven material.

12. The body fluid absorbent structure of claim 9, wherein said depressed areas are provided at least in those areas of said structure which receive moisture discharged from the wearer's body.

* * * * *

UNITED STATES PATENT AND TRADEMARK OFFICE
CERTIFICATE OF CORRECTION

PATENT NO. : 4,041,951
DATED : August 16, 1977
INVENTOR(S) : Lawrence H. Sanford It is certified that error appears in the above-identified patent and that said Letters Patent are hereby corrected as shown below:

```
Column 2, line 19, "layer", second occurrence, should
read -- liquid --.

Column 3, line 3, "wearer'skin" should read -- wearer's
skin --.

Column 5, line 34, "depressd" should read -- depressed --.

Column 7, lines 11 and 12, "resume" should read --
reassume --.

Column 9, line 57, "wer" should read -- were --.

Column 11, line 5, "moisture-previous" should read --
moisture-pervious --.
```

Signed and Sealed this

Twenty-fifth Day of July 1978

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,041,951
DATED : August 16, 1977
INVENTOR(S) : Lawrence H. Sanford It is certified that error appears in the above–identified patent and that said Letters Patent are hereby corrected as shown below:

Column 9, line 41, "positions" should read -- portions --.

Signed and Sealed this

Twenty-fourth Day of November 1981

[SEAL]

Attest:

Attesting Officer

GERALD J. MOSSINGHOFF

Commissioner of Patents and Trademarks